US007601756B2

(12) United States Patent
Mueller

(10) Patent No.: US 7,601,756 B2
(45) Date of Patent: Oct. 13, 2009

(54) METHOD OF TREATMENT FOR IRRITABLE BOWEL SYNDROME

(75) Inventor: Peter Sterling Mueller, Princeton, NJ (US)

(73) Assignee: Snowden Pharmaceuticals, LLC, Princeton, NJ (US)

( * ) Notice: Subject to any disclaimer, the term of this patent is extended or adjusted under 35 U.S.C. 154(b) by 0 days.

(21) Appl. No.: 10/861,308

(22) Filed: Jun. 4, 2004

(65) Prior Publication Data

US 2004/0248980 A1    Dec. 9, 2004

Related U.S. Application Data

(60) Provisional application No. 60/476,777, filed on Jun. 6, 2003.

(51) Int. Cl.
*A61K 31/192*    (2006.01)
*A61K 31/216*    (2006.01)

(52) U.S. Cl. ...................... 514/543; 514/571

(58) Field of Classification Search ............ None
See application file for complete search history.

(56) References Cited

U.S. PATENT DOCUMENTS

| | | | |
|---|---|---|---|
| 3,262,850 A | 7/1966 | Jones et al. ............... 167/65 |
| 3,674,836 A | 7/1972 | Creger .................. 260/410.9 |
| 3,781,328 A | 12/1973 | Witte et al. ............... 260/471 |
| 3,948,973 A | 4/1976 | Phillips .................. 260/473 |
| 4,058,552 A | 11/1977 | Mieville .................. 560/52 |
| 4,895,726 A | 1/1990 | Curtet et al. ............. 424/456 |
| 6,074,670 A | 6/2000 | Stamm et al. ............. 424/462 |
| 6,277,405 B1 | 8/2001 | Stamm et al. ............. 424/462 |
| 6,399,640 B1 * | 6/2002 | Sahoo et al. ............. 514/369 |
| 6,525,083 B2 * | 2/2003 | Acton et al. ............. 514/415 |
| 6,569,879 B2 * | 5/2003 | Liu et al. ................. 514/373 |
| 6,589,552 B2 | 7/2003 | Stamm et al. ............. 424/457 |
| 6,652,881 B2 | 11/2003 | Stamm et al. ............. 424/462 |
| 6,713,508 B2 * | 3/2004 | Sahoo et al. ............. 514/456 |
| 2001/0028895 A1 | 10/2001 | Bisgaier et al. ........... 424/450 |
| 2002/0013334 A1 | 1/2002 | Robl et al. ............... 514/291 |
| 2002/0042441 A1 | 4/2002 | Acton, III et al. ........ 514/415 |
| 2002/0055529 A1 | 5/2002 | Bisgaier et al. ........... 514/369 |
| 2002/0103242 A1 | 8/2002 | Sahoo et al. ............. 514/379 |
| 2002/0173663 A1 | 11/2002 | Liu et al. ................. 548/207 |
| 2003/0045553 A1 | 3/2003 | Bussolari et al. ........ 514/340 |
| 2003/0092736 A1 | 5/2003 | Cheng et al. ............. 514/333 |

FOREIGN PATENT DOCUMENTS

WO    WO 03/059294    7/2003

OTHER PUBLICATIONS

The Merck Index, 17th edition (1999) p. 208.*
Camilleri et al.; The Irritable Bowel Syndrome: Mechanisms and a Practical Approach to Management; Annals of Internal Medicine; vol. 116, No. 12 (Part I); Jun. 15, 1992, pp. 1001-1008.
Fruchart et al.; Consensus for the Use of Fibrates in the Treatment of Dyslipoproteinemia and Coronary Heart Disease; The American Journal of Cardiology; vol. 81; Apr. 1, 1998; pp. 912-917.
Adkins et al.; Micronised Fenofibrate; Drugs; vol. 54 (4); Oct. 1997; pp. 615-633.
Fibric Acid Derivatives; http://www.drugdigest.org/DD/Comparison/New Comparison/0,10621,35-15,00.html; (2003 Express Scripts, Inc.) (as printed on Jun. 2, 2003).
Rosenson; Lipid Lowering with Fibric Acid Derivatives; http://www.uptodate.com/patient_info/topicpages/topics/LipidDis/7385.asp?usd=98622024... (as printed on Jun. 2, 2003).
Hoffmann-La Roche Ltd./Ltee; Product Monograph-Bezallip®; Date of Preparation: Mar. 18, 1994; Date of Revision: Jan. 29, 2002; pp. 1-11.
Lopid®; Information for Health Professionals Data Sheet; http://www.medsafe.govt.nz/profs/Datasheet/l/Lopidcaptab.htm; (as printed on Jun. 3, 2003).
Kolata; New Evidence Cites Overactive Nerves for Irritable Bowel; The New York Times Medical Science; Tuesday, Feb. 2, 1988.
Dr. Peter H. Gott, Family Doctor; IBS affects people of all ages; Trenton Times; Jul. 26, 2003.
Drossman et al.; The Irritable Bowel Syndrome: Review and a Graduated Multicomponent Treatment Approach; Annals of Internal Medicine; vol. 116, No. 12 (Part 1); Jun. 15, 1992; pp. 1009-1016.
Almy; Management of the Irritable Bowel Syndrome; Different Views of the Same Disease; Annals of Internal Medicine; vol. 116; No. 12 (Part 1); Jun. 15, 1992; pp. 1027-1028.
Christensen; Pathophysiology of the Irritable bowel syndrome; The Lancet; vol. 340; Dec. 12, 1992; pp. 1444-1447.
Schreiber et al.; Recombinant Erythropoietin for the Treatment of Anemia in Inflammatory Bowel Disease; The New England Journal of Medicine; vol. 334, No. 10; Mar. 7, 1996; pp. 619-682.
Lydiard; Anxiety and the Irritable Bowel Syndrome: Psychiatric, Medical, or Both?; J Clin Psychiatry; vol. 58, (suppl 3); 1997; pp. 51-58.
Wender et al.; Prevalence of Attention Deficit Disorder, Residual Type, and Other Psychiatric Disorders in Patients With Irritable Colon Syndrome; Am J Psychiatry; vol. 140:12; Dec. 1983; pp. 1579-1582.
Hendricks; Bowels in an Uproar; John Hopkins Magazine; Apr. 1997; pp. 20-25.
Press Release; Cypress Bioscience Holds Kick-Off Meeting for New Clinical Study Using Milnacipran to Treat Irritable Bowel Syndrome; Cypress Bioscience, Inc.; San Diego, CA, Jun. 25, 2003.
Press Release: Cypress Bioscience Revises Milnacipran License with Pierre Fabre Medicament to Improve Economic Terms and Expand the Licensed Field; Cypress Bioscience, Inc.; San Diego, CA; Jun. 9, 2003.
Press Release: Cypress Bioscience, Inc.'s Announces Topline Final Results of Milnacipran Phase II Study in Fibromyalgia Syndrome; Cypress Bioscience, Inc.; San Diego, CA; Feb. 10, 2003.
Fruchart et al.; Consensus for the use of fibrates in the treatment of dyslipoproteinemia and cornory heart disease; Am J Cardiology; vol. 81 (7); Apr. 1, 1998; pp. 912-917 (MEDLINE Abstract).

(Continued)

*Primary Examiner*—Phyllis G. Spivack
(74) *Attorney, Agent, or Firm*—Hoffman & Baron, LLP

(57) ABSTRACT

A method for treating irritable bowel syndrome (IBS) is included. The method includes the step of administering a fibric acid derivative to a patient diagnosed with IBS in order to alleviate the symptoms associated with IBS.

10 Claims, No Drawings

OTHER PUBLICATIONS

Weber et al.; Clinical approaches to irritable bowel syndrome; The Lancet; vol. 340; Dec. 12, 1992; pp. 1447-1452.

Badgett; Diagnosing the Irritable Bowel Syndrome; Annals of Internal Medicine; vol. 117, No. 12; Dec. 15, 1992; pp. 1056-1057.

Monk et al., Bezafibrate, A review of its pharmacodynamic and pharmacokinetic properties, and therapeutic use in hyperlipidamia; Drugs, Vo. 33 (6), Jun. 1987; pp. 539-576 (MEDLINE Abstract).

Drug Digest, Fibric Acid Derivatives; http://drugdigest.com/DD/PrintablePages/Comparisons/1,20038,35-15,00.html; Updated Aug. 2004.

WebMD Health; Clofibrate; http://my.webmed.com/content/drugs/1/4046_1219?bn=Atromid%2ds, (as printed on Jun. 2, 2003).

HealthSquare; Lopid; http://www.healthsquare.com/newrx/lop1234.htm; last revised Mar. 18, 2003 (as printed on Jun. 2, 2003).

Athyros, Vasilios G., M.D., et al., "Atorvastatin and Micronized Fenofibrate Alone and in Combination in Type 2 Diabetes with Combined Hyperlipidemia", Diabetes Care, vol. 25, No. 7, 1198-1202 (Jul. 2002).

Mayer, Emeran A., M.D., "Irritable Bowel Syndrome", N. Engl. J. Med., 358, 16, 1692-1699 (Apr. 17, 2008).

* cited by examiner

METHOD OF TREATMENT FOR IRRITABLE BOWEL SYNDROME

CROSS-REFERENCE TO RELATED APPLICATION

This application claims the benefit of U.S. Provisional Application No. 60/476,777, filed Jun. 6, 2003, the contents of which are incorporated herein by reference.

FIELD OF THE INVENTION

The present invention relates to methods for treating the symptoms of irritable bowel syndrome. Specifically, a fibric acid derivative is administered to a person exhibiting such symptoms.

BACKGROUND OF THE RELATED TECHNOLOGY

Only the common cold outranks Irritable Bowel Syndrome (IBS) as a cause of absenteeism from work. Thirty percent of individuals suffering from IBS miss at least one day of work per month on average. However, there is no medication on the market today that is an effective treatment for IBS.

Although IBS includes a variety of specific symptoms, there is no direct test that will determine whether someone has the condition. Normally, a variety of tests are performed to rule out other diseases. For example, a colonoscopy is frequently performed to rule out inflammatory bowel disease and testing for lactose intolerance also is performed.

Stress and other psychological considerations have been found to exacerbate the symptoms of those who suffer from IBS. This has led some physicians to treat IBS as a purely psychosomatic disorder and to look for an underlying psychiatric disorder. As a result, many physicians look for an additional psychiatric disorder to treat. For example, some of those who have IBS also have been diagnosed with Attention Deficit Disorder (ADD), post traumatic stress disorder (PTSD), and/or general anxiety disorder (GAD), a social phobia including agoraphobia or depression. This has led some physicians to believe that IBS is a result of the psychiatric disorder and that treating the psychiatric disorder also will cure the IBS. However, this is clearly an erroneous contention considering that only about one-half of those with IBS also have a psychiatric disorder.

Although IBS is clearly an independent condition, the fact that its symptoms are magnified by psychiatric factors leads doctors to still treat IBS as part of a psychiatric disorder. Considering that the overwhelming majority of those who seek treatment for IBS symptoms do have a psychiatric disorder in addition to the IBS, the psychiatric medical treatment is not unreasonable. However, some physicians have suggested that even when IBS patients do not have a psychiatric disorder, treatment with psychiatric medications is an acceptable practice. They have based this theory on the fact that administration of drugs such as anti-depressants and psychotropic agents to those with IBS without psychiatric disorder have experienced an improvement in symptoms. However, as mentioned above, this reduction in symptoms is from the treatment of the aggravating factors, such as stress, but is not the result of directly treating IBS. Furthermore, many psychiatric medications have undesirable side effects.

Therefore, there is a need for a treatment for those suffering from IBS. Desirably, the medication will not have the unfavorable side effects associated with many psychiatric medications. Most desirably, the treatment will have positive side effects, such as reducing the patient's level of bad cholesterol.

SUMMARY OF THE INVENTION

One aspect of the invention includes a method for treating irritable bowel syndrome (IBS) which includes the step of administering an effective amount of a fibric acid derivative (also known as a fibrate) to a person afflicted with IBS. Any of a variety of fibric acid derivatives are useful with the present invention. Examples of suitable fibric acid derivatives correspond to the following formula:

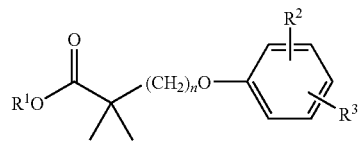

wherein
$R^1$ is H, substituted $C_{1-4}$ alkyl, or unsubstituted $C_{1-4}$ alkyl;
n is 0, 1, 2, or 3;
$R^2$ is H, substituted $C_{1-4}$ alkyl, unsubstituted $C_{1-4}$ alkyl, or halogen;
$R^3$ is H, substituted $C_{1-4}$ alkyl, unsubstituted $C_{1-4}$ alkyl, $C_{3-6}$ cycloalkyl, unsubstituted $C_{3-6}$ cycloalkyl, halogen, —$COR^4$, or —$(CH_2)_2NHCOR^4$;
$R^4$ is phenyl or substituted phenyl; and
each substitution is independently selected from the group consisting of halogen and $C_{1-4}$ alkyl.

Commercially available fibric acid derivatives include clofibrate, fenofibrate, gemfibrozil, bezafibrate, and ciprofibrate. One or more fibric acid derivatives is useful with the methods of the present invention.

DETAILED DESCRIPTION OF THE INVENTION

Fibric acid derivatives have previously been used to lower lipid levels, leading to a variety of benefits such as plaque stabilization, reversal of endothelial dysfunction, and decreased thrombogenicity. More specifically, fibric acid derivatives have been found to lower serum triglycerides and raise high density lipoprotein (HDL) (a.k.a. "good cholesterol"). In the United States, currently available fibric acid derivatives include gemfibrozil, fenofibrate, and clofibrate. Other fibric acid derivatives include bezafibrate and ciprofibrate.

The fibric acid derivatives useful in the present invention may include one or more compounds of the following formula:

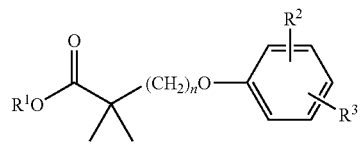

wherein
$R^1$ is H, substituted $C_{1-4}$ alkyl, or unsubstituted $C_{1-4}$ alkyl;
n is 0, 1, 2, or 3;
$R^2$ is H, substituted $C_{1-4}$ alkyl, unsubstituted $C_{1-4}$ alkyl, or halogen;

$R^3$ is H, substituted $C_{1-4}$ alkyl, unsubstituted $C_{1-4}$ alkyl, $C_{3-6}$ cycloalkyl, unsubstituted $C_{3-6}$ cycloalkyl, halogen, —$COR^4$, or —$(CH_2)_2NHCOR^4$;

$R^4$ is phenyl or substituted phenyl; and each substitution is independently selected from the group consisting of halogen and $C_{1-4}$ alkyl.

For the purposes of the present invention, the following definitions will apply:

Alkyl is meant to include any straight or branched chain alkyl moiety. For $C_{1-4}$ alkyl, this includes methyl, ethyl, propyl, isopropyl, butyl, isobutyl, and tertbutyl. Substituted alkyl means that each carbon atom may have up to three substituents depending on its position in the chain.

Cycloalkyl is meant to include saturated or unsaturated hydrocarbon ring systems. $C_{3-6}$ cycloalkyl includes cyclopropyl, cyclobutyl, cyclopentyl, and cyclohexyl groups. A substituted cycloalkyl group may include up to two substituents depending on its position in the ring.

Phenyl is meant to include a six-membered aromatic ring, which also may be substituted at any of the ortho, meta, and para positions.

Each substituted moiety as described above may include substituents that are selected from halogen (F, Cl, Br, and I) and $C_{1-4}$ alkyl.

The fibric acid derivative also may be micronized, e.g. micronized fenofibrate, which may increase the bioavailability of the medication. A method of preparing micronized fenofibrate is disclosed in U.S. Pat. Nos. 4,895,726, 6,074,670, and 6,277,405 all of which are incorporated herein by reference in their entirety.

The amount of the medication that is prescribed will depend on which fibric acid derivative is used. Generally, the administration may be from one to about four times per day. The amount which is administered daily will be from about 1 mg to about 6 mg per pound of body weight.

Each of the commercially available fibric acid derivatives is discussed below:

Fenofibrate

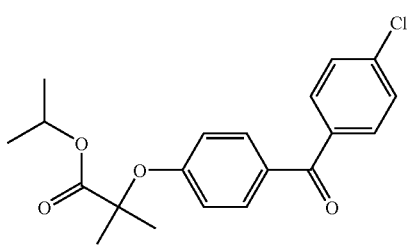

2-(4-(4-chlorobenzoyl)phenoxy)-2-methyl-propanoic acid 1-methyl ethyl ester

Fenofibrate (2-(4-(4-chlorobenzoyl)phenoxy)-2-methyl-propanoic acid 1-methyl ethyl ester) is available commercially as Tricor® by Abbott Laboratories and in micronized form as Lofibra® by Teva Pharmaceuticals. The dosage depends on whether the micronized form is used. If the micronized form is used, the dosage will be 200 mg either once, twice or thrice daily. Otherwise, the dosage will be about 300 mg daily divided into two or more administrations.

Methods of preparing fenofibrate and other fibric acid derivatives which are useful in the methods of the present invention are included in U.S. Pat. No. 4,058,552, herein incorporated by reference in its entirety.

Gemfibrozil

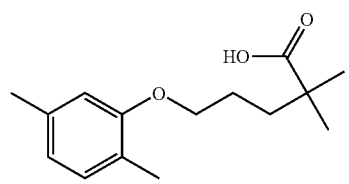

5-(2,5-dimethylphenoxy)-2,2-dimethylpentanoic acid

Gemfibrozil (5-(2,5-dimethylphenoxy)-2,2-dimethylpentanoic acid) is commercially available under the trademark Lopid® by Pfizer and also in generic form from Geneva Pharmaceuticals, Lederle, Mylan, Teva, Torpharm and Watson Labs. Administration is generally about 600 mg to 1200 mg daily in one or two administrations.

Methods of preparing gemfibrozil and other fibric acid derivatives which are useful in the methods of the present invention are included in U.S. Pat. No. 3,674,836, herein incorporated by reference in its entirety.

Clofibrate

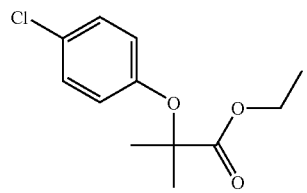

2-(4-chlorophenoxy)-2-methyl-propanoic ethyl ester

Clofibrate (2-(4-chlorophenoxy)-2-methyl-propanoic ethyl ester) is available under the trademark Atromid-S® by Wyeth Ayerst, but is also available in generic form by Banner, Teva, and USL Pharma. The dosage varies between 500 mg to 1500 mg daily divided in one to three administrations.

Methods of preparing clofibrate and other fibric acid derivatives which are useful in the methods of the present invention are included in U.S. Pat. No. 3,262,850, herein incorporated by reference in its entirety.

Bezafibrate

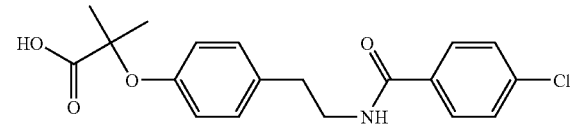

2-(4-(2-(4-chloro-benzoylamino)-ethyl)phenoxy)-2-methyl-propanoic acid

Bezafibrate (2-(4-(2-(4-chloro-benzoylamino)-ethyl)phenoxy)-2-methyl-propanoic acid) is not available in the United States at this time. However, in Canada, it is available as Bezalip® by Hoffmann-La Roche as a 400 mg sustained release tablet which is administered once or twice daily.

Methods of preparing bezafibrate and other fibric acid derivatives which are useful in the methods of the present invention are included in U.S. Pat. No. 3,781,328, herein incorporated by reference in its entirety.

Ciprofibrate

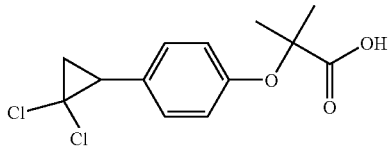

2-(4-(2,2-dichlorocyclopropyl)phenoxy)-2-methyl propanoic acid

Ciprofibrate (2-(4-(2,2-dichlorocyclopropyl)phenoxy)-2-methyl propanoic acid) also is not available in the United States at this time. However, it is available from Sanofi-Synthélabo, a French company, under the trademarks Lipanor® and Modalim®. The dosage is about 100 mg daily.

Methods of preparing fenofibrate and other fibric acid derivatives which are useful in the methods of the present invention are included in U.S. Pat. No. 3,948,973, herein incorporated by reference in its entirety.

The features and advantages of the present invention are more fully shown by the following examples which are provided for purposes of illustration, and are not to be construed as limiting the invention in any way.

EXAMPLES

The following examples include the case studies of individuals who have received treatment under the methods of the present invention. Table 1 shows each patient's evaluation of his or her symptoms in several categories which correspond to different symptoms which afflict sufferers of IBS. These symptoms, which are self-explanatory, include gas, cramps/pain, diarrhea, mucus, and constipation. Each patient subjectively evaluated his or her symptoms both before and after treatment on a scale from 0 to 10 with 0 representing the absence of symptoms and 10 indicating the most severe symptoms. Both evaluations are included.

TABLE 1

PATIENT EVALUATION OF SYMPTOMS

| Patient | Age | Sex | Gas | Cramps/Pain | Diarrhea | Mucus | Constipation | Overall |
|---------|-----|-----|-----|-------------|----------|-------|--------------|---------|
| 1       | 37  | M   |     |             |          |       |              |         |
| Before  |     |     | 4   | 8           | 9        | 8     | 0            | 6.5     |
| After   |     |     | 1   | 1           | 1        | 2     | 0            | 1       |
| 2       |     | M   |     |             |          |       |              |         |
| Before  |     |     | 4.5 | 5           | 8.5      | 0     | 0            | 9       |
| After   |     |     | 0   | 0           | 0        | 0     | 3            | 1       |
| 3       | 35  | F   |     |             |          |       |              |         |
| Before  |     |     | 3   | 7           | 9        | 3     | 0            | 7       |
| After   |     |     | 1   | 2           | 3        | 0     | 0            | 2       |

Example 1

Patient 1 suffered from a variety of conditions including diabetes, post traumatic attention deficit disorder, and irritable bowel syndrome. Testing revealed that Patient 1 also had an elevated triglyceride level and low HDL (high density lipoprotein) level. As can be seen from Table 1, Patient 1 evaluated his IBS symptoms overall as 6.5, with particular severity of symptoms relating to cramps/pain, diarrhea, and mucus.

Patient 1 was treated with Gemfibrozil 600 mg twice a day and his evaluation of symptoms changed from the before ratings to the after ratings within a day, which indicates significant improvement. When Patient 1 discontinued use of the Gemfibrozil, his symptoms returned to the before levels. However, upon resuming the Gemfibrozil treatment, the levels were again reduced. Later testing revealed that Patient 1's HDL level also increased after treatment, which is a beneficial side effect.

Example 2

Patient 2 originally suffered from attention deficit disorder (ADD), some depression, and IBS. His IBS symptoms were so severe that he was afraid of leaving his home for fear of unavailability of restroom facilities. His evaluation of these symptoms is shown in Table 1.

Patient 2 also was treated with Gemfibrozil 600 mg twice daily. As is shown in Table 1, Patient 2's symptoms virtually disappeared after only 1.5 days of treatment. Patient 2 did experience occasional constipation, but given his history, he considered this a welcome change. The treatment resulted in a vastly increased quality of life as he was now able to leave his home without fear of his symptoms returning.

Example 3

Patient 3 was diagnosed as having IBS, with no additional disorder. Her initial evaluation of symptoms is shown in Table 1.

Patient 3 was originally treated with Gemfibrozil 600 mg twice daily. The improvement in symptoms shown in Table 1 is after 2 days of treatment. As can be seen, her symptoms were greatly improved. However, her treatment was then discontinued and a new treatment, micronized fenofibrate 200 mg daily was then introduced. After the fenofibrate treatment, Patient 3's evaluation of symptoms was at 0 in all categories.

While there have been described what are presently believed to be the preferred embodiments of the invention, those skilled in the art will realize that changes and modifications may be made thereto without departing from the spirit of the invention, and it is intended to include all such changes and modifications as fall within the true scope of the invention.

What is claimed is:

1. A method for treating irritable bowel syndrome consisting essentially of the step of administering to a patient afflicted with irritable bowel syndrome an effective amount of a compound selected from the group consisting of fenofibrate, gemfibrozil and combinations thereof.

2. The method of claim 1, wherein said compound is in micronized form.

3. The method of claim 1, wherein said compound is micronized fenofibrate.

4. The method of claim 1, wherein said effective amount of said compound comprises about 1 mg to about 6 mg per pound of body weight.

5. The method of claim 1, wherein the compound is administered from about once to about four times daily.

6. The method of claim 1, wherein the compound is gemfibrozil.

7. The method of claim 6, wherein 600 mg of gemfibrozil is administered.

8. The method of claim 1, wherein the compound is fenofibrate.

9. The method of claim 8, wherein 300 mg of fenofibrate is administered daily.

10. The method of claim 8, wherein 200 mg of fenofibrate or micronized fenofibrate is administered once or twice or thrice daily.

* * * * *